US00PP14120P29

(12) United States Plant Patent
Kolster

(10) Patent No.: US PP14,120 P2
(45) Date of Patent: Sep. 2, 2003

(54) COTINUS PLANT NAMED 'KOLCOT'

(75) Inventor: Pieter Kolster, Boskoop (NL)

(73) Assignee: Gebr. Kolster B.V., Boskoop (NL)

( * ) Notice: Subject to any disclaimer, the term of this patent is extended or adjusted under 35 U.S.C. 154(b) by 0 days.

(21) Appl. No.: 10/159,060

(22) Filed: May 31, 2002

(51) Int. Cl.[7] ..... A01H 5/00

(52) U.S. Cl. ..... Plt./226

(58) Field of Search ..... Plt./226

(56) References Cited

PUBLICATIONS

UPOV–ROM GTITM Computer Database 2002/06, GTI Jouve Retrieval Software, Citation for 'Kolcot'.*

* cited by examiner

*Primary Examiner*—Bruce R. Campell
*Assistant Examiner*—Annette H. Para
(74) *Attorney, Agent, or Firm*—C. A. Whealy

(57) ABSTRACT

A new and distinct cultivar of Cotinus plant named 'Kolcot', characterized by its upright and outwardly spreading plant habit; freely branching growth habit; dark green-colored leaves; early and freely flowering habit; and large showy and feathery inflorescences.

1 Drawing Sheet

BOTANICAL CLASSIFICATION/CULTIVAR DESIGNATION

*Continus coggygria* cultivar Kolcot.

BACKGROUND OF THE INVENTION

The present Invention relates to a new and distinct cultivar of Cotinus plant, botanically known as *Cotinus coggygria*, and hereinafter referred to by the name 'Kolcot'.

The new Cotinus was discovered as a cross-pollination of two unidentified selections of *Cotinus coggygria,* not patented. The new Cotinus was discovered and selected by the Inventor in 1998 as a single flowering plant in a controlled environment in Boskoop, The Netherlands, within a population of the progeny resulting from the cross-pollination.

Asexual reproduction of the new Cotinus by cuttings was first conducted in Boskoop, The Netherlands in 1998. Since then, asexual reproduction by cuttings has shown that the unique features of this new Cotinus are stable and reproduced true to type in successive generations.

SUMMARY OF THE INVENTION

The cultivar Kolcot has not been observed under all possible environmental conditions. The phenotype may vary somewhat with variations in environment such as temperature and light intensity without, however, any variance in genotype.

The following traits have been repeatedly observed and are determined to be the unique characteristics of 'Kolcot'. These characteristics in combination distinguish 'Kolcot' as a new and distinct Cotinus:

1. Upright and outwardly spreading plant habit.
2. Freely branching growth habit.
3. Dark green-colored leaves.
4. Early and freely flowering habit.
5. Large showy and feathery inflorescences.

Plants of the new Cotinus differ primarily from plants of the parent selections primarily in growth habit and foliage coloration.

Plants of the new Cotinus can be compared to plants of the Cotinus cultivar Royal Purple, not patented. In side-by-side comparisons conducted in Boskoop, The Netherlands, plants of the new Cotinus differed from plants of the cultivar Royal Purple in the following characteristics:

1. Plants of the new Cotinus were more freely branching than plants of the cultivar Royal Purple.

2. Plants of the new Cotinus had green-colored leaves whereas plants of the cultivar Royal Purple had red-colored leaves.

3. Plants of the new Cotinus flowered during the first growing season whereas plants of the cultivar Royal Purple did not flower until after the first growing season.

BRIEF DESCRIPTION OF THE PHOTOGRAPH

The accompanying colored photograph illustrates the overall appearance of the new Cotinus showing the colors as true as it is reasonably possible to obtain in colored reproductions of this type. Colors in the photograph may differ from the color values cited in the detailed botanical description which accurately describe the colors of the new Cotinus. The photograph comprises a side perspective view of a typical two-year flowering plant of 'Kolcot' grown in an outdoor nursery in Boskoop, The Netherlands.

DETAILED BOTANICAL DESCRIPTION

The aforementioned photographs and following observations and measurements describe plants grown in Boskoop, The Netherlands, in an outdoor nursery under full sun conditions. The photographs and the observations and measurements were taken in June, 2001; plants used for the observations and measurements were about 16 months old. During June, day temperatures averaged 17° C. and night temperatures averaged 10° C. Color references are made to The Royal Horticultural Society Colour Chart, 2001 edition, except where general terms of ordinary dictionary significance are used.

Botanical classification: *Cotinus coggygria* cultivar Kolcot.

Parentage:

*Female, or seed, parent.*—Unidentified selection of *Cotinus coggygria,* not patented.

*Male, or pollen, parent.*—Unidentified selection of *Cotinus coggygria,* not patented.

Propagation:

*Type.*—By cuttings.

*Time to initiate roots.*—About 45 days at 17° C.

*Time to produce a rooted plant.*—About 100 days at 17° C.

*Root description.*—Fine, dense.

Plant description:

*Appearance.*—Perennial woody shrub. Upright and outwardly spreading plant habit; rounded broad inverted triangle. Very freely branching; about ten basal branches with about 12 lateral branches develop per plant; dense and full plants. Moderately vigorous growth habit.

*Plant height.*—About 50 cm.

*Plant width or area of spread.*—About 30 cm.

*Lateral branches.*—Length: About 10 cm. Diameter: About 3.5 mm. Internode length: About 1 cm. Strength: Strong. Texture: Glabrous. Color, immature: 144A. Color, mature: 199A to 199B.

*Foliage description.*—Arrangement: Alternate; single. Length: About 5.5 cm. Width: About 4 cm. Shape: Broadly obovate. Apex: Rounded. Base: Attenuate. Margin: Entire. Venation pattern: Pinnate. Texture, upper and lower surfaces: Smooth, glabrous. Color: Young foliage, upper surface: 146A. Young foliage, lower surface: 146B to 147B. Fully expanded foliage, upper surface: 137A. Fully expanded foliage, lower surface: 137C. Venation, upper and lower surfaces: 143C. Petiole: Length: About 1.2 cm. Diameter: About 1 mm. Texture, upper and lower surfaces: Glabrous. Color, upper and lower surfaces: 143C.

Flower description:

*Appearance.*—Small single cup-shaped flowers arranged in loose, feathery, showy and large terminal panicles held above and beyond the foliage. Flowers face mostly upright. Flowers not persistent.

*Flowering response.*—Plants flower continuous and freely during the early summer, mid-June to early July in Boskoop, The Netherlands. Plants of the new Cotinus start flowering during the first growing season.

*Postproduction longevity.*—Individual flowers maintain good color and substance for about two days on the plant when grown in an outdoor environment.

*Quantity of flowers.*—Freely flowering; about 150 open inflorescences and buds per lateral stem per flowering season.

*Fragrance.*—None detected.

*Flower bud.*—Length: About 1.5 mm. Diameter: About 2 mm. Shape: Flattened globular. Color: 144A.

*Inflorescence size.*—Length: About 13 cm. Diameter: About 8 cm.

*Flowers.*—Diameter: About 2 mm. Height (depth): About 1.5 mm.

*Petals.*—Quantity per flower: Five. Length: About 1 mm. Width: About 1 mm. Shape: Broadly ovate. Apex: Acute. Base: Attenuate. Margin: Entire. Texture, upper and lower surfaces: Smooth. Color: Developing and fully expanded petals, upper surface: N144A. Developing and fully expanded petals, lower surface: N144A.

*Sepals.*—Quantity per flower: Five. Length: About 1 mm. Width: About 1 mm. Shape: Broadly ovate. Apex: Acute. Base: Broadly cuneate. Margin: Entire. Texture, upper and lower surfaces: Smooth. Color: Developing and fully expanded sepals, upper surface: 144A. Developing and fully expanded sepals, lower surface: 144A.

*Peduncles.*—Length: About 1.7 cm. Diameter: About 1 mm. Orientation: About 80 to 110° from vertical. Strength: Moderately strong. Color: N144A.

*Pedicels.*—Length: About 1 cm. Diameter: About 0.75 mm. Orientation: About 110 to 280° from vertical. Strength: Moderately strong. Color: N144A.

*Reproductive organs.*—Stamens: Quantity per flower: About six. Anther shape: Globular; basifixed. Anther length: About 0.2 mm. Anther color: Close to 3A. Pollen amount: Scarce. Pollen color: Close to 3A. Pistils: Quantity per flower: Three; fused towards base. Pistil length: About 5 mm. Stigma shape: Club-shaped. Stigma color: Close to 202A. Style length: About 5 mm. Style color: Close to 137A. Ovary color: 137A.

*Fruits.*—Quantity per flower: One. Days to ripening: About 20. Longevity on the plant: More than two weeks. Type: Drupe. Length: About 4 mm. Diameter: About 3 mm. Texture: Smooth, glabrous. Color: 187B.

*Seed.*—Length: About 1 mm. Diameter: About 0.5 mm. Texture: Smooth, glabrous. Color: Close to 200A.

Disease resistance: Plants of the new Cotinus have not been observed to be resistant to pathogens common to Cotinus.

Temperature tolerance: Plants of the new Cotinus have been observed to tolerate temperatures from about −23 to 38° C.

It is claimed:

1. A new and distinct cultivar of Cotinus plant named 'Kolcot', as illustrated and described.

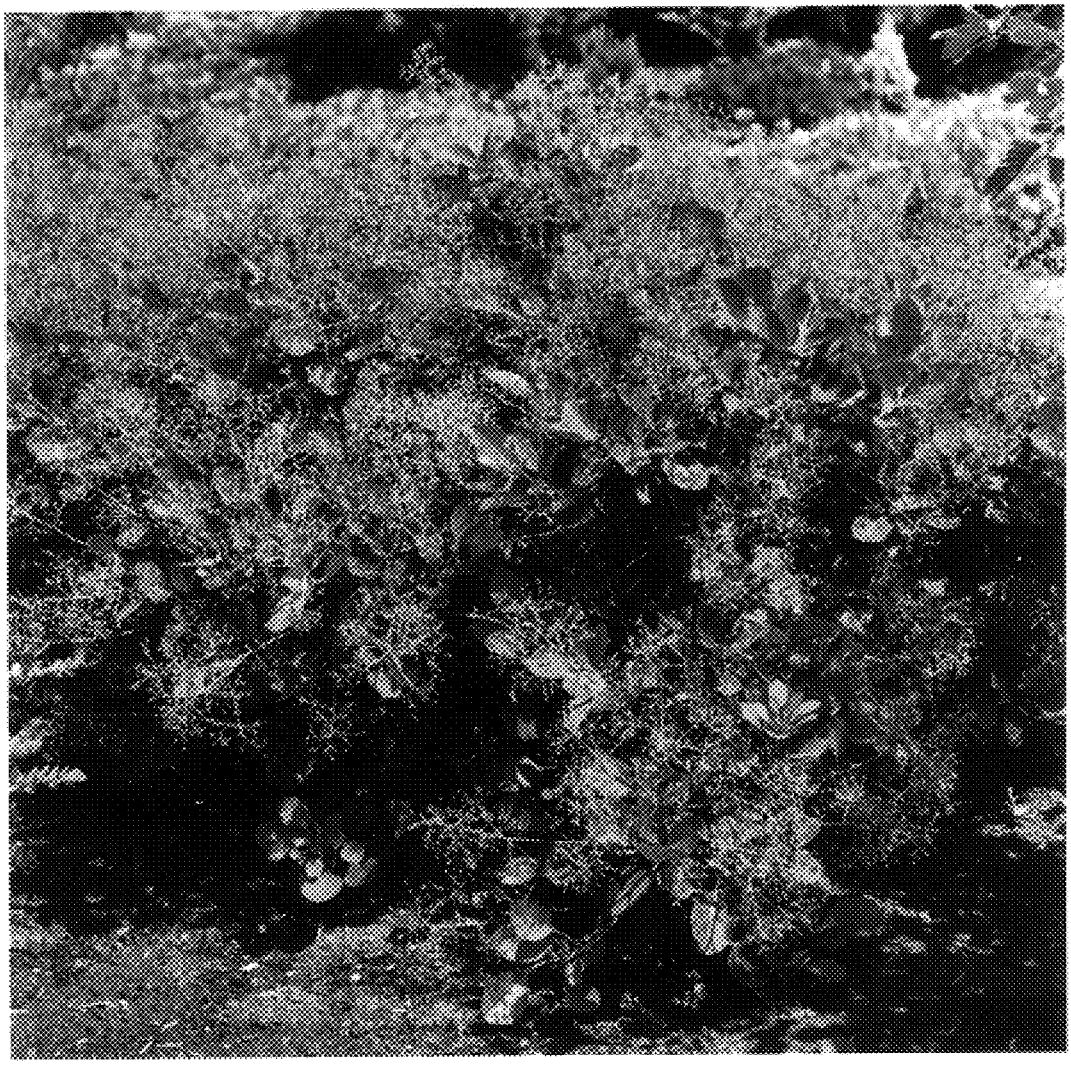

* * * * *